(12) United States Patent
Heiser

(10) Patent No.: US 6,942,483 B2
(45) Date of Patent: Sep. 13, 2005

(54) ORTHODONTIC BRACKET

(76) Inventor: Wolfgang Heiser, Dr.-Stumpf-Strasse 73, A-6020 Innsbruck (AT)

( * ) Notice: Subject to any disclaimer, the term of this patent is extended or adjusted under 35 U.S.C. 154(b) by 0 days.

(21) Appl. No.: 10/788,101

(22) Filed: Feb. 26, 2004

(65) Prior Publication Data
US 2004/0170942 A1 Sep. 2, 2004

(30) Foreign Application Priority Data

Feb. 27, 2003 (DE) ......................................... 103 08 795
May 27, 2003 (DE) ......................................... 103 24 088

(51) Int. Cl.⁷ ................................................. A61C 7/00
(52) U.S. Cl. ....................................................... 433/11
(58) Field of Search ............................ 433/11, 8, 9, 10, 433/13, 14

(56) References Cited

U.S. PATENT DOCUMENTS

| | | | |
|---|---|---|---|
| 4,023,274 A | * | 5/1977 | Wallshein ..................... 433/11 |
| 4,144,642 A | | 3/1979 | Wallshein |
| 4,492,573 A | | 1/1985 | Hanson |
| 4,712,999 A | * | 12/1987 | Rosenberg ..................... 433/8 |
| 5,562,444 A | | 10/1996 | Heiser et al. |
| 5,711,666 A | * | 1/1998 | Hanson ........................ 433/11 |

* cited by examiner

*Primary Examiner*—Melba Bumgarner
(74) *Attorney, Agent, or Firm*—Jansson, Shupe, Munger & Antaramian, Ltd.

(57) ABSTRACT

A bracket for orthodontic treatments comprises a closing spring, which is fixedly anchored at the bracket and which covers an arch wire slot formed in the bracket for receiving an arch wire in a closed position. In an end section of the closing spring covering the slot, a tongue is formed in the center and folded at an angle toward a base plate of the bracket. The spring has an end section which is held by projections formed at the bracket structure to secure the spring in its closed position. The spring may be dimensioned and pre-tensioned in a manner that an arch wire inserted into the slot is torqued by the closing spring with forces from the top and from the side.

19 Claims, 5 Drawing Sheets

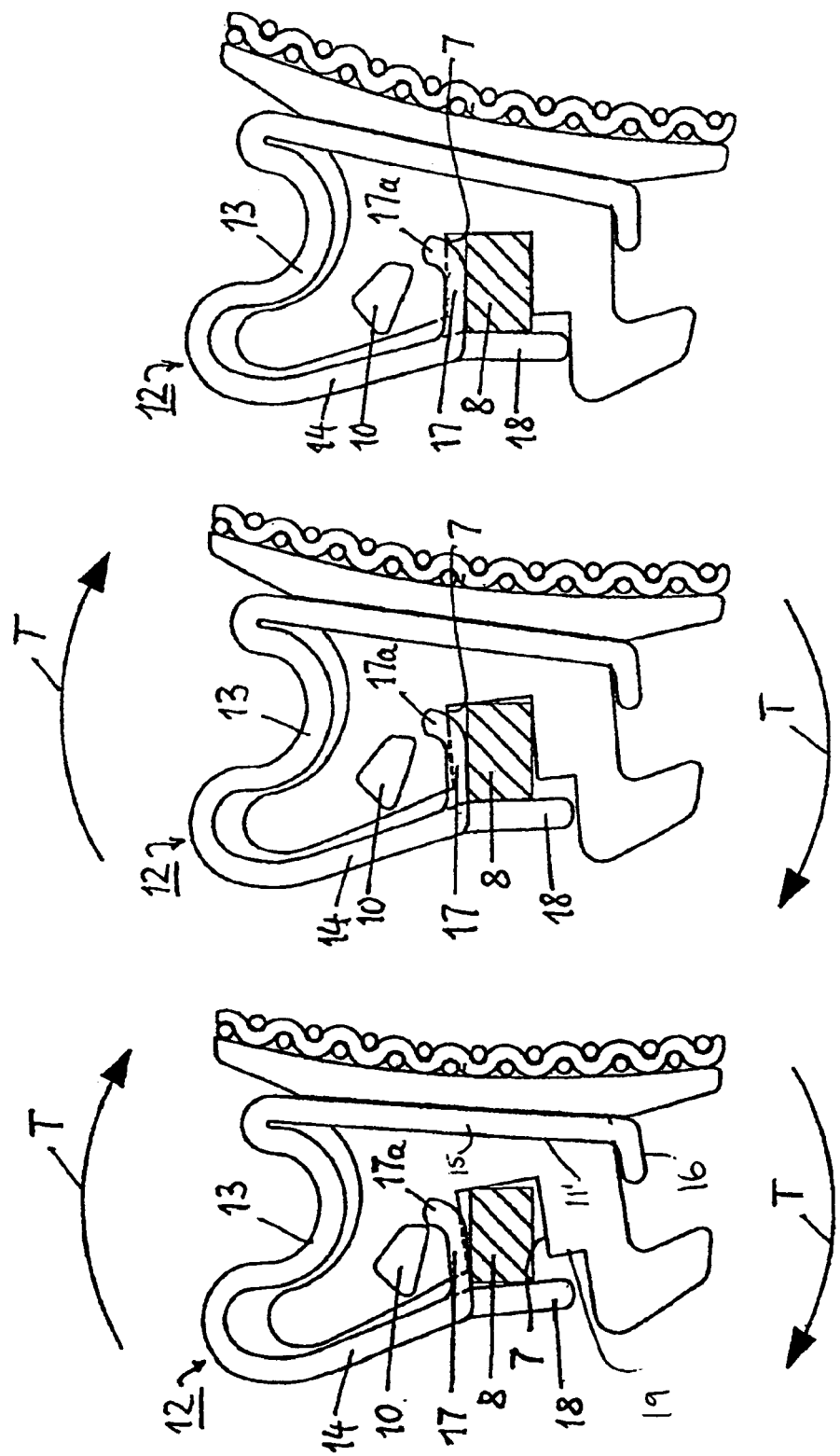

ORTHODONTIC BRACKET

RELATED APPLICATION

This application claims the benefit of DE 103 08 795.8, filed on Feb. 27, 2003, and DE 103 24 088.8, filed May 27, 2003, the contents of which are incorporated herein.

FIELD OF THE INVENTION

The present invention relates to brackets for orthodontic treatments, and, more particularly to such brackets which are mounted to teeth and moved via tension in a wire.

BACKGROUND OF THE INVENTION

A bracket of the type involving a base plate having a top and bottom side adapted to be attached to a tooth, two spaced apart wings arranged on the top side with an elongate slot extending therethrough for receiving an arch wire, and a closing spring made of a band-like material, anchored to the structure and movable between an open position in which the slot is freely accessible in an area between the wing sections and a closing position in which the free leg of the spring covers the slot is known, for instance, from U.S. Pat. No. 5,562,444. In the known bracket, an elongate leg is formed at the end of the arc of the closing spring with the free end of the leg being positioned in a broad groove formed on the bottom side of the gingival wing sections covered by the arc of the spring. This groove has a great opening angle which allows pivoting of the closing spring around the gingival wing sections between an open and a closed position, wherein the apex of the groove forms a pivot bearing together with the edge of the free end of the leg arranged in the groove. In the opening and closing positions, the spring holds on to the gingival wing sections covered by the spring by its inherent spring force by clamping effect.

However, it turned out in practice that when carelessly opening the spring the spring's elasticity limit can be exceeded so that the retention force by which it usually holds on to the gingival wing sections of the bracket structure is weakened. It can therefore easily get lost since the clamping force of the spring at the wing sections is the only means by which the spring holds onto its place.

In the above-mentioned reference, another bracket is described as including a spring which has an elongation at the end of the arc which does not cover the slot, with the elongation being bifurcated into two legs that are received by channels which extend laterally in the bracket structure below the slot and transversely thereto. In this bracket, there is also the risk of bending the spring too far, since only an arc of approximately 180° arc length is available for the bending process when opening the spring.

A bracket similar to the last mentioned bracket is known from U.S. Pat. No. 4,492,573, in which the bracket comprises an essentially U-shaped bent closing spring, the entirety of which, when opening the slot, can be moved transversely to the slot.

U.S. Pat. No. 4,144,642 also describes a bracket having a clip spring which can be shifted transversely with respect to the slot when opening and closing the slot for receiving the arch wire.

All the above-mentioned brackets have springs which, if they exert a force onto an arch wire inserted into the slot at all, exert a force directed towards the bottom of the slot, i.e., their springs press the arch wire towards the bottom of the slot. The spring force for each of these brackets is determined by the rigidity of the spring material and the effective spring length. The effective spring length is relatively great in all of these examples since it corresponds to the distance between the clamping location of the spring and the engagement location at the arch wire. Only when the spring rigidity is sufficiently great is sufficient closing force of the spring generated, which in turn enlarges the risk of a plastic deformation of the spring when moving it into the opening position.

Furthermore, a closing spring which only presses the arch wire on the bottom of the slot is less suitable for obtaining a torque which turns a treated tooth around an axis which extends through the level of the crown of the tooth.

SUMMARY OF THE INVENTION

It is the object of the invention to provide a bracket of the above-mentioned type, which is capable of generating a high closing force for securing an arch wire in the bracket slot without increasing the risk of damage of the spring during opening. The bracket may possibly also be capable of developing a high torque around an axis located on the level of a tooth crown.

This object may be attained according to the invention in a bracket as set forth in the opening portion of this specification by providing that the gingival wing sections of the structure covered by the arc of the closing spring have a projection on the sides facing each other. Such projections preferably have free ends which face each other at a predetermined distance. The free leg of the closing spring preferably has a central tongue-like section which is angled with respect to the free leg substantially at a right angle in the direction toward the upper side of the base plate and has a free end section with a width that is smaller than the distance between the opposing sides of the gingival wing sections but is larger than the distance between the free ends of the projections. The remainder of the tongue-like section is preferably not wider than the width of the free end section.

The free end section may be bent in the direction toward the arc of the closing spring so that it grips below a lower edge of the projections when in the closed position of the closing spring.

The lateral sections of the free ends of the closing spring adjacent to the tongue-like section, for the sake of simplicity referred to as tongue, are resilient lugs which are parallel to each other and which extend across the slot in the bracket structure to secure an arch wire positioned in the slot. Since the free end section of the tongue grips the projections, the closing and securement of the closing spring is almost exclusively determined by the tongue, the projections and the resilient lugs, so that the securement of the arch wire within the slot is substantially independent of the properties of the spring arc enclosing the gingival wing sections.

The free end section of the tongue may have a width which is larger than the distance between the projections, whereas an adjoining neck portion of the tongue may have a width which is smaller than such distance. The tongue of this type is adapted in a manner such that in the closed position of the spring, the end section is situated below the projections while the neck portion extends between the projections. Thus, the tongue positively secures the spring in its closed position without requiring that the end section be kept in a bent state.

Since the dimensions of the lugs and tongue are relatively small, their effective spring length is also relatively small. In order to enlarge the effective spring length of the tongue and lugs, a non-angled section may be provided in the root portion of the tongue on the free leg of the closing spring such that longitudinally extending slots separate the non-angled section from the free leg.

The closing spring comprises an extension leg preferably at an end of the arc distal of the free leg, the extension leg preferably being fixedly anchored on the structure. For this purpose, a flat continuous channel extending through the structure may be formed in the structure above the top side of the base plate but underneath the arch wire reception slot to receive the extension leg of the spring, which is formed smaller than the arc. The extension leg preferably extends through the channel and projects its free end from the channel, where it is folded to secure the extension leg, and thus the entire closing spring, onto the structure. As an alternative, an insertion slot may be provided in the structure underneath the wing covered by the arc of the spring, with the extension leg being inserted into the insertion slot and secured therein by welding, soldering or caulking.

It is also advantageous if an opening is formed in the closing spring adjacent to the tongue. This hole is provided for receiving a tool in the form of a needle which is used for opening the closing spring by plugging it into the hole and releasing the end of the tongue from its catch underneath the projections.

According to a preferred embodiment of the invention, a shoulder may be formed on the incisal wing sections of the structure, i.e., the sections which are not covered by the arc of the closing spring. Such shoulders are positioned adjacent to the slot. The lateral sections of the free leg of the closing spring, i.e., the above-mentioned resilient lugs, can rest on these shoulders in the closed position of the closing spring.

If the closing spring is tensioned to prefer the closed position, it can nonetheless be secured in the open position by providing the projections at the gingival wing sections with a top side which is obliquely inclined from an apex edge extending in the direction away from the arch wire slot. The free end of the angled tongue can be supported on this inclined surface in the open position of the closing spring. However, the spring can also be designed, or tensioned, to have an inherent preference for the open position. Such a spring can be held against this pre-tension in the closed position by the bent end section of the tongue which grips underneath the projections on the gingival wing sections or by the wide end section of the tongue disposed beneath the projections, depending on the embodiment of the tongue.

In order to enable opening and closing of the spring even when using arch wires which have cross sections that fill the entire width of the slot, the projections are spaced from the slot by a slight distance which is at least as large as the thickness of the closing spring, thereby allowing the tongue to be engaged by the projections without contacting the arch wire.

DESCRIPTION OF THE DRAWINGS

The invention will now be described in detail with reference to the embodiments shown in the drawings.

FIGS. 11, 12 and 13 show cross sectional views of an alternative embodiment of a bracket with an arch wire of a rectangular cross section inserted into the slot to demonstrate the torque effect that the arch wire may cause in cooperation with the closing spring;

DETAILED DESCRIPTION OF THE INVENTION

The invention will now be explained in detail with reference to the drawings.

Figure 1:
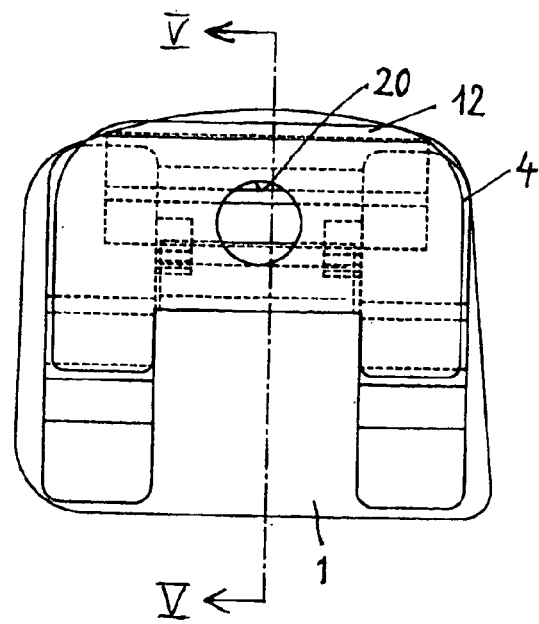
FIG. 1 shows a plan view of an embodiment of a complete bracket.
Figure 2:
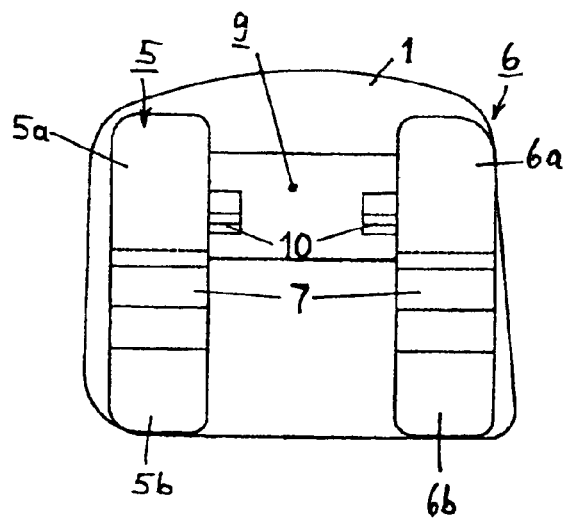
FIG. 2 shows a plan view of the base plate and the structure of the bracket of FIG. 1 elevating therefrom.
Figure 3:
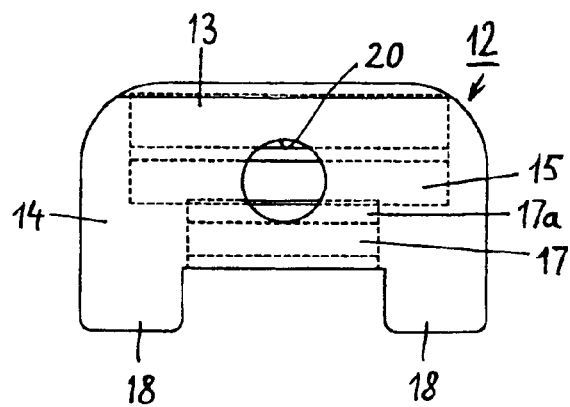
FIG. 3 shows a plan view of the closing spring for the bracket according to FIGS. 1 and 2.

As shown in FIGS. 1 to 3, the bracket consists of a base plate 1, which comprises a bottom side 2 (see FIG. 5) and a top side 3 from which a structure 4 arises.

The base plate 1 has an irregular contour, since this contour is adapted to the contour of the crown of a tooth at which the specially shown bracket is adapted to be attached.

Figure 5:
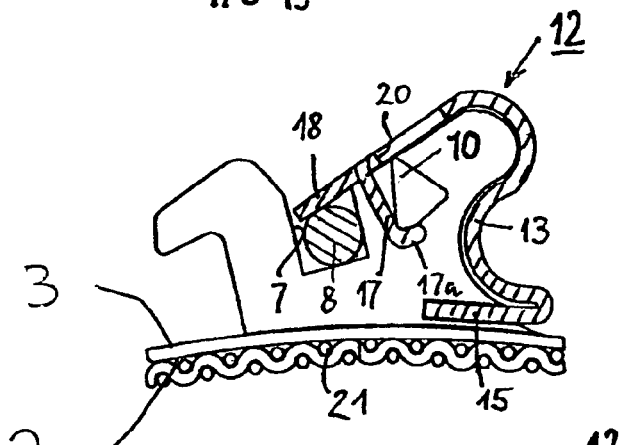
FIG. 5 shows a cross sectional view of the bracket of FIG. 1 cut along line V—V with an arch wire having a round cross section inserted into the slot, the arch wire not being shown in FIG. 1 for reasons of clarity.
Figure 6:
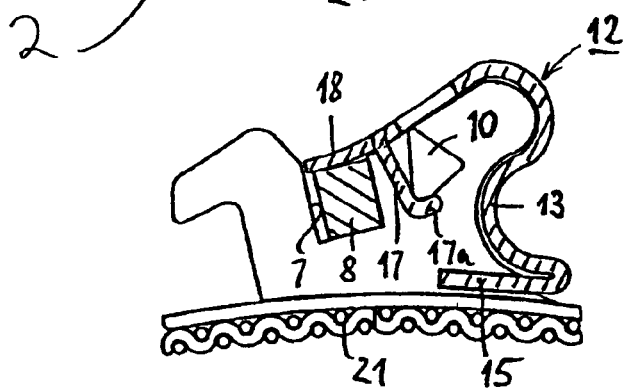
FIG. 6 shows a cross sectional view similar to FIG. 5 with an arch wire of a rectangular cross section inserted into the slot.
Figure 7:
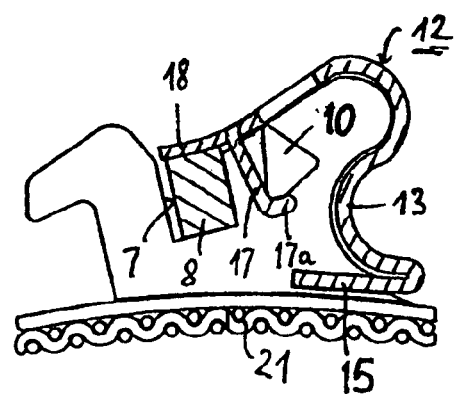
FIG. 7 shows a cross sectional view similar to FIG. 5 with an arch wire of a rectangular cross section and an enlarged height inserted into the slot.

The structure 4 has two mesial and distal wings 5 and 6 opposing each other at a mutual distance and divided into gingival and incisal sections 5a, 6a and 5b, 6b, respectively. For example, sections 5a and 5b are easily discerned in FIG. 15 which shows mesial wing 5. Sections 5a and 5b are separated from one another by a slot 7 extending between them which is adapted to receive an arch wire 8. Examples of such arch wires are shown in FIGS. 5 to 7. In the following, slot 7 is called arch wire slot.

Figure 15:
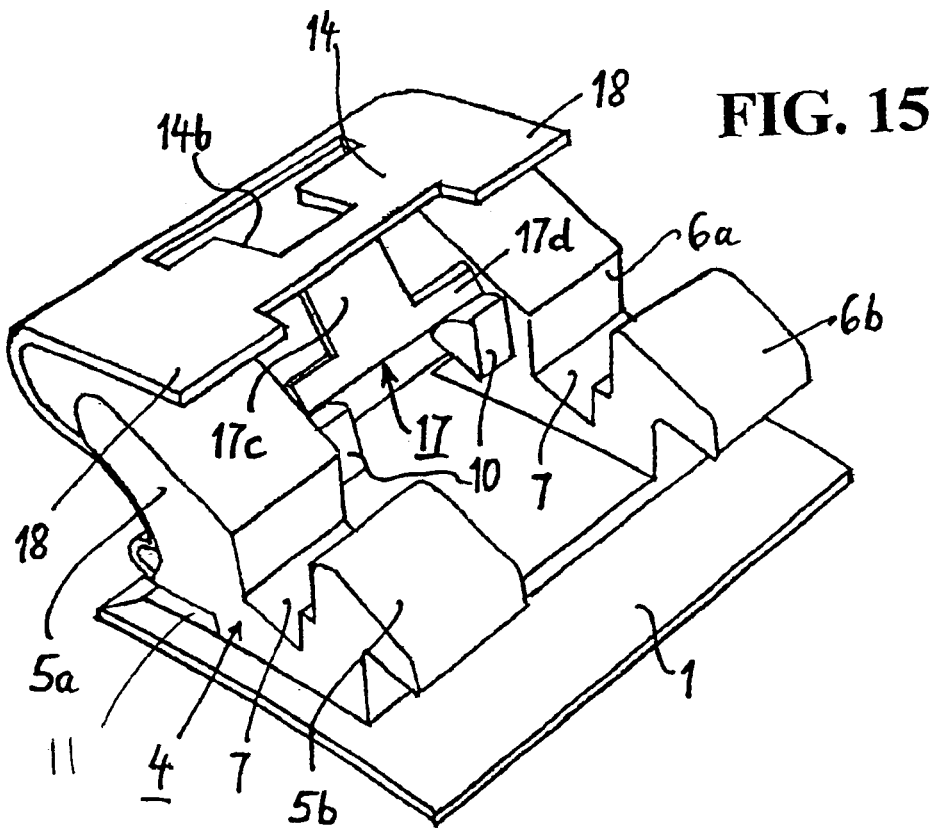
FIG. 15 is a perspective view of the bracket of FIG. 14, showing the bracket with its spring in the open position.

Gap 9 separates the mesial and distal wings 5 and 6 from one another as shown in FIG. 2 and extends close to top side 3 of base plate 1, as seen in FIG. 15. Two nose-like projections 10 extend from gingival wing sections 5a, 6a toward each other and into gap 9.

In the gingival section of structure 4 a flat channel 11 (shown in FIGS. 14 and 15) is formed above base plate 1, extends into the central portion of structure 4 and is adapted to receive an end of a closing spring belonging to the bracket. Details will be explained below.

Gingival wing sections 5a and 6a of structure 4 are covered by the already mentioned closing spring, which is designated by reference numeral 12. Closing spring 12 is shown as a single member in FIGS. 3 and 4. Closing spring 12 has an arc portion 13 extending in several arcs connected at one end to a free, substantially straight end portion 14 and at the other, lower end to a straight extension 15, which is formed narrower than the remainder of closing spring 12. Extension 15 is inserted into channel 11 in structure 4 and secured therein by welding, soldering or caulking. Closing spring 12 may be made of metal or of plastics.

Figure 4:
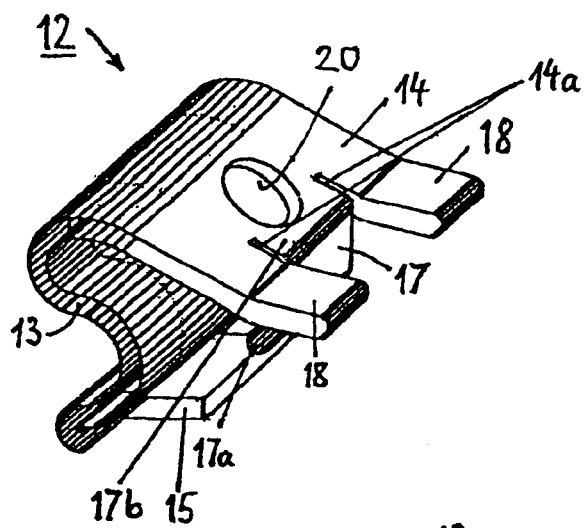
FIG. 4 shows a perspective view of an embodiment of the closing spring having a tongue with an enlarged effective length.

Straight end portion 14 has a tongue 17 in its central portion, the tongue being free of connection on both sides from the material of closing spring 12 and being folded toward base plate 1 of the bracket, as clearly shown in FIG. 4. When closing spring 12 is in the closed position, tongue 17 adjoins slot 7 in gap 9. Tongue 17 has an end section 17a bent backwards, which lies below the edge of projections 10 when spring 12 is closed. Lateral lugs 18 of straight end portion 14 of closing spring 12 cover arch wire slot 7 and an arch wire (FIG. 5) inserted therein. The distance between the gingival wall laterally restricting arch wire slot 7 and projection 10 is at least as large as the thickness of the material of closing spring 12.

Closing spring 12 has an opening 20 that is adapted to be penetrated by a needle or pin-like tool which may for instance be formed similar to a crochet hook.

In an advantageous embodiment, which is shown in FIG. 4, tongue 17 of closing spring 12 has a section 17b in its root portion where tongue 17 is connected to free leg 14 and is not angled with respect to free leg 14, but is delimited on both sides by a longitudinally extending slot or recess 14a. By these slots 14a, the effective length of tongue 17 is enlarged without the other dimensions of closing spring 12 being changed. The enlargement of the effective tongue length helps to avoid a plastic deformation or breaking of tongue 17 when inserting or changing an arch wire. Moreover, the effective lengths of lugs 18, which form the free end of the closing spring 12, are also enlarged to further counteract a plastic deformation.

It can clearly be seen in FIG. 5 that closing spring 12 is captively secured at the bracket structure, and as a result of the design of arcuate section 13 closing spring 12 can be bent out very far without the risk of closing spring 12 being expanded beyond its elasticity limit, i.e., without it being overstretched.

Nevertheless, arch wire 8 is effectively secured when inserted into the arch wire slot 7. This securing effect is effected mainly by tongue 17 and lugs 18, rather than by spring arc 13. As may be seen, lower end section 17a of tongue 17 grips underneath projections 10 and holds spring 12 in the closed position. Two lugs 18 extend from the root of tongue 17 and over arch wire 8 disposed in arch wire slot 7. The entire holding and securing function is consequently performed in the area around tongue 17, i.e., by lugs 18 and projections 10, thereby alleviating the need for the remaining spring to have an important influence thereon. Thus, it is even possible to employ closing spring 12 under pre-tension, in which closing spring 12 reaches its relieved state when in the open position, since closing spring 12 is held in its closed position by tongue 17 once it was brought into this position.

The basic structure of the bracket, consisting of base plate 1 and structure 4, is preferably manufactured by casting or injection molding of metal or suitable plastic material. Closing spring 12 is positioned by inserting extension 15 into channel 11, where it is secured in the manner already described.

It must also be noted that bottom side 2 of base plate 1 is adapted to be attached at the crown of a tooth by means of an adhesive or cement. This adhesive or cement is schematically shown in FIGS. 5 to 7 by reference numeral 21.

Another advantage of the invention can be seen in FIGS. 6 and 7, as compared to FIG. 5. In FIG. 5, an arch wire 8 having a round cross section is inserted into arch wire slot 7, with the arch wire not filling the cross section of the slot. Lugs 18 of closing spring 12 rest in a substantially tensionless manner on arch wire 8. In FIG. 6, an arch wire 8 of a rectangular cross section is inserted into arch wire slot 7, the wire filling the slot in its full height. This leads to the result that lugs 18 of closing spring 12 bend slightly upwards when closing spring 12 is secured in the closed position by locking lower tongue end 17a underneath projections 10. As shown in FIG. 7, an arch wire 8 of a rectangular cross section inserted into slot 7 rises above the upper edge of slot 7. This leads to the result that lugs 18 are bent even further upward if spring 12, as shown, is secured in the closed position. As shown by the drawings, the remainder of closing spring 12 remains fully unaffected by this securing arrangement in the area of the slot.

Figure 8:
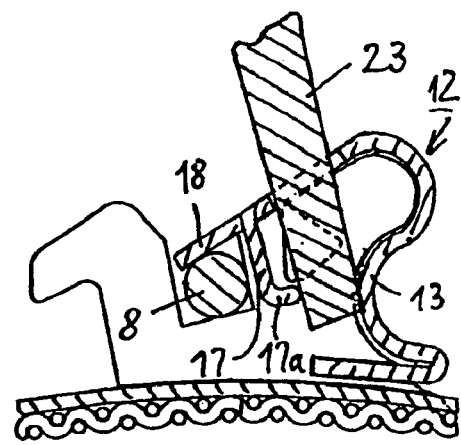
FIG. 8 shows a view comparable to the view of FIG. 5 with an inserted opening tool at the beginning of the opening process.
Figure 9:
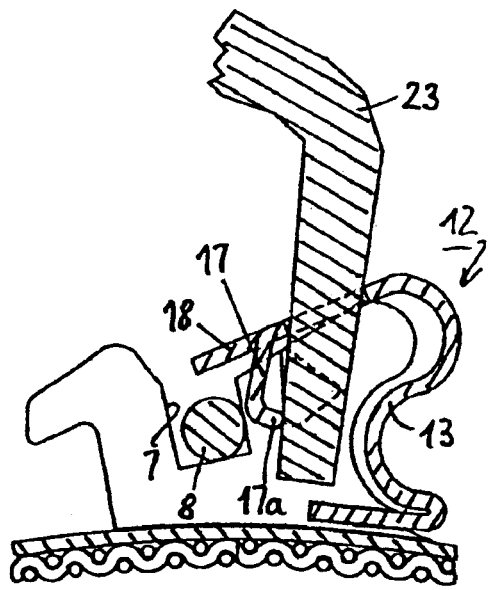
FIG. 9 shows a view similar to FIG. 8 during progress of the opening process.
Figure 10:
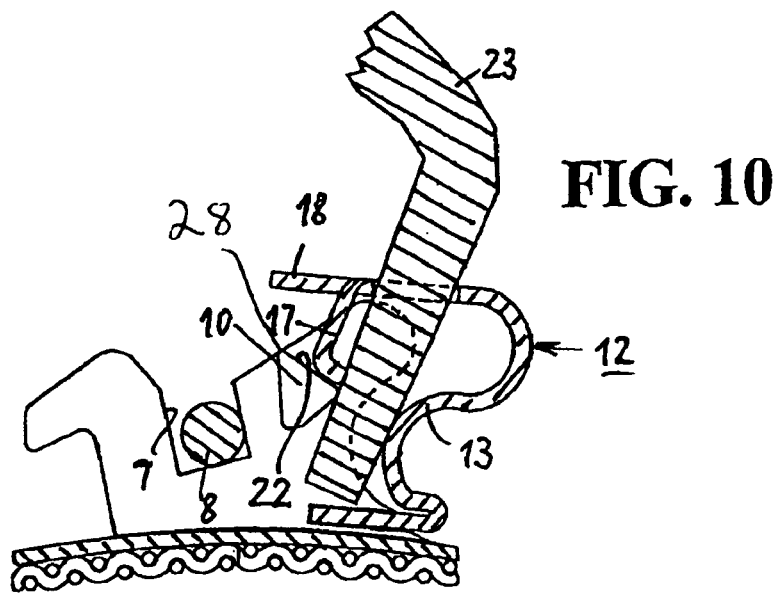
FIG. 10 shows a view similar to FIGS. 8 and 9 at the end of the opening process.

With reference to FIGS. 8 to 10 further advantages of the invention and the process of opening closing spring 12 are explained. For reasons of clarity, hatched lines typically used in sectional views are not shown.

FIG. 8 shows the bracket with an inserted arch wire of a round cross section (as an example) in a state comparable to that shown in FIG. 5. The backward bent end section 17a of the unlatched tongue 17 of closing spring 12 lies below the lower edges of projections 10, i.e., below the edge of projections 10 nearest base plate 1. Lugs 18 of closing spring 12 rest next to arch wire 8. A pin-like tool 23 is inserted into opening 20, the tool being capable of being inserted between projections 10. Tool 23 contacts the free edge of folded end section 17a of tongue 17.

In FIG. 9, tool 23 has been pressed against the free edge of folded end section 17a of tongue 17 and has freed the tongue from the catch position below projections 10. By slightly tilting tool 23 further, closing spring 12 can be tilted further away from projections 10 so that lugs 18 freely release slot 7 (FIG. 10). If closing spring 12 is bent sufficiently backwards, lower, folded end section 17a of tongue 17 can rest on the top side of each projection 10. If each top side 22 has a suitable inclination extending from apex edge 28 in a direction away from arch wire slot 7, projections 10 are capable of holding closing spring 12 in the open position shown in FIG. 10 even if closing spring 12 has a pretension effective in the closing direction.

As an alternative, closing spring 12 may have a pre-tension effective in the opening direction. In such cases, a support for tongue 17 on projections 10 is not necessary. In any case, it can be seen from these two alternatives that any certain pre-tension of closing spring 12 is not important for securing arch wire 8 with lugs 18 and tongue 17. The design and arrangement of lugs 18, tongue 17 and projections 10 are the decisive factor.

In FIG. 11, an alternative embodiment, which deviates from the shown and described bracket by two independent features, is shown. In this bracket, a shoulder 19 adjoins at the upper end of arch wire slot 7 on the incisal side, with lugs 18 being able to rest on this shoulder. When an arch wire 8 does not have sufficient thickness to fill arch wire slot 7, lugs 18 will contact shoulder 19 and will not press onto arch wire 8.

The second deviating feature refers to closing spring 12 which has an extension 15 on the lower end of arc 13 which is so long that it fully penetrates a flat through channel 11' formed in the bracket structure transversely to slot 7, projects therefrom, and is secured to the bracket structure by folding spring end 16.

A further advantage shown in FIG. 11 in combination with FIGS. 12 and 13 which can be achieved by the bracket according to the invention is that tongue 17 can be used together with a pre-tension of closing spring 12 as an instrument for exerting directional forces at an arch wire.

FIGS. 11 to 13 show the bracket according to the invention when being used with an arch wire 8 of a rectangular cross section. Arch wires with a rectangular cross section are typically used at the end of an orthodontic treatment with brackets if the misalignment of the teeth was corrected to such an extent that arch wires of a smaller cross section, particularly of a round cross section, are no longer able to cause those torques at the teeth that are required for bringing the teeth to the desired final position.

In the course of an orthodontic treatment it may be necessary to pivot the teeth not only around a horizontal axis located in the root portion but possibly around a horizontal axis located in the area of the tooth crown. An arch wire of a rectangular cross section may in combination with a bracket whose arch wire slot also has a rectangular cross section cause at the tooth provided with this bracket a torque that lies in the region of the tooth crown. This will be explained with reference to FIGS. 11 to 13.

A series of brackets are provided on a row of teeth of the upper jaw and the arch wire extends through the arch wire slots of all brackets. The arch wire's position within the slots is therefore not only determined by the individual brackets but by the cooperation of all brackets, the positions of which are determined by the position of all teeth in the respective row of teeth. Thus, the teeth align each other by the forces mutually acting at the arch wire.

In FIG. 11, arch wire 8 is canted in slot 7 due to the misalignment of the tooth (not shown) provided with the bracket shown so that wedge-shaped gaps result between the outer faces of arch wire 8 and the surfaces defining slot 7. Closing spring 12 exerts forces by means of lateral lugs 18 and tongue 17 onto arch wire 8, which intend to press the wire onto the bottom of arch wire slot 7 and in abutment with the slot wall opposing tongue 17. These forces result in a torque which is exerted onto the bracket (shown in FIG. 11 by arrows T.)

With the progressing effect of this torque T onto the tooth provided with the bracket, the tooth slightly yields so that the canting of arch wire 8 within arch wire slot 7 becomes smaller. This reduced state of the cant is shown in FIG. 12. With further progress of the influence of the torque a state is finally obtained, shown in FIG. 13, in which the bottom surface of arch wire 8 planarly rests on the bottom of arch wire slot 7 and the side surface of arch wire 8 rests planarly on the limiting wall of arch wire slot 7 opposing tongue 17. The consequence is that the position of the bracket in FIG. 11 was changed into a preferred inclined position according to FIG. 13. Thus, the position of the tooth to which the bracket is attached was changed accordingly.

Figure 14:
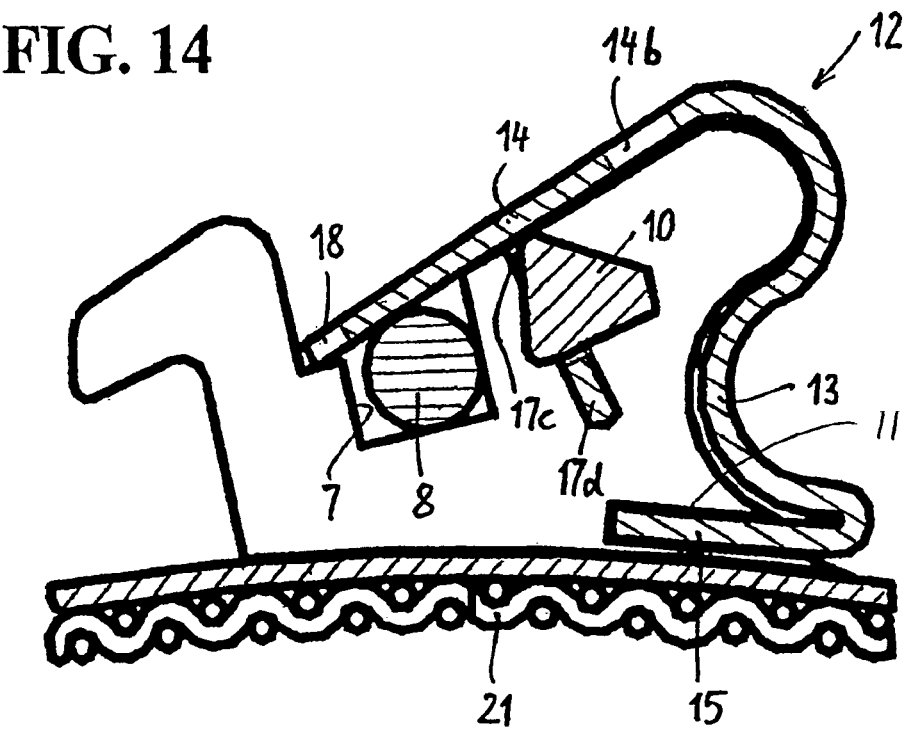
FIG. 14 is a cross sectional view of another embodiment of a bracket in which its spring has a tongue with the end section disposed beneath the projections.

FIGS. 14 and 15 show a particularly preferred embodiment of the invention. As may clearly be seen from FIG. 15, in this embodiment tongue 17 has a neck section 17c adjoining the tongue root, the neck section 17c having a width which is smaller than the distance between projections 10 at gingival wing sections 5a, 6a, i.e., smaller than the width of the gap between gingival wing sections 5a, 6a. An end section 17d adjoins to neck section 17c and has a width which is larger than the distance between projections 10, but is smaller than the width of the gap between gingival wing sections 5a, 6a. Tongue 17 is flat and is partially cut out from free leg 14 of closing spring 12 and bent in a direction toward the bottom of the bracket and to the front, so that a T-shaped opening 14b is formed by partially cutting-out free leg 14.

As is shown in FIG. 15, wide end section 17d of tongue 17 is able to rest on projections 10 in the open position of closing spring 12 so that the latter is held in its open position. On the other hand, when moving closing spring 12 into its closed position, shown in FIG. 14, neck portion 17c can pass between projections 10 so that wide end section 17d of tongue 17 reaches a resting position below projections 10 and locks closing spring 10 in its closed position. The orthodontist may unlock the spring by inserting a pin-shaped tool through T-shaped opening 14b of spring 14 to push end section 17d of tongue 17 out of its locked position, so that end section 17d may slide over the surfaces of projections 10 close to arch wire slot 7.

The broader end section 17d of tongue 17 may be bent in a manner as shown in the embodiments first explained above. Further, in the embodiment of FIGS. 14 and 15, tongue 17 may be formed at free leg 14 of spring 12 in a manner as is explained with respect to the first mentioned embodiments and shown in FIG. 4.

Finally, it should be mentioned that all wing sections may have projections or protrusions in opposing directions, as shown in the drawings, which make it possible to attach ligatures at the bracket in the usual manner, if desired. Attachment of ligatures is often desired at the beginning of an orthodontic treatment when the pressure of closing spring 12 acting on the arch wire is not sufficiently high to effect a safe retainment of the arch wire in the arch wire slot.

While the principles of the invention have been shown and described in connection with specific embodiments, it is to be understood that such embodiments are by way of example and are not limiting.

What is claimed is:

1. A bracket for an orthodontic treatment, the bracket comprising:

a wing for operative connection to a tooth, the wing having a wire slot for receiving an arch wire, the wire slot dividing the wing into a first and second section, the first section having a projection extending therefrom; and a closing spring anchored with respect to the wing and comprising an arc extending over the first section and a free leg adjoining the arc, the closing spring being movable between an open position, in which the arch wire slot is freely accessible, and a closed position, in which the arch wire slot is covered, the free leg including a lug and a tongue depending at an angle from the free leg, the lug covering the arch wire slot and the tongue being engaged by the projection when the closing spring is in the closed and open position, the tongue and projection retaining the spring in the closed and open position.

2. The bracket of claim 1 wherein the bracket further comprises a base plate having a top and bottom side, the top side attached to the wing and the bottom side capable of being attached to the tooth.

3. The bracket of claim 2 wherein the wing includes a channel and the spring includes a fixed end adjacent the arc opposite the free end, the fixed end being received and fixed in the channel.

4. The bracket of claim 1 wherein the closing spring has an extension leg on an end of the arc opposite the free leg, the extension leg being fixedly anchored with respect to the wing.

5. The bracket of claim 4 further including a channel formed between the wing and a top side of a base plate, the channel receiving the extension leg of the closing spring, and wherein the extension leg includes a projecting end which projects from the channel and substantially perpendicular to the channel to secure the extension leg in the channel.

6. The bracket of claim 4 further including an insertion slot formed below the first section, the insertion slot receiving the extension leg, the extension leg secured thereto by one of welding, soldering and caulking.

7. The bracket of claim 1 wherein a shoulder is formed on the second section adjacent the arch wire slot, the lug resting on the shoulder when the closing spring is in the closed position.

8. A bracket for an orthodontic treatment, the bracket comprising:

two wings for operative connection to a tooth, the wings spaced apart from each other by a gap, the wings defining a wire slot for receiving an arch wire, the wire slot dividing the wings into first and second sections, each first section having a projection extending into the gap; and a closing spring anchored with respect to the wings and comprising an arc extending over the first sections and a free leg adjoining the arc, the closing spring being movable between an open position, in which the arch wire slot is freely accessible, and a closed position, in which the arch wire slot is covered by a portion of the closing spring, the free leg including a tongue depending at an angle therefrom and two lugs adjacent the tongue, the lugs covering the arch wire slot and the tongue being engaged by the projections when the closing spring is in the closed position, the tongue and projections retaining the spring in the closed position.

9. The bracket of claim 8 wherein the lugs contact the arch wire when the closing spring is in the closed position to cause torque adjustment of the tooth.

10. The bracket of claim 8 wherein the tongue includes an engagement section having a width which is less than the gap between the first sections and greater than the distance between the projections, the engagement section being engaged by the projections when the closing spring is in the closed position.

11. The bracket of claim 10 wherein the engagement section includes a bent portion which is bent toward the arc, the bent portion being positioned below and engaged by the projections when the closing spring is in the closed position.

12. The bracket of claim 10 wherein the tongue includes a neck portion having a width which is less than the distance between the projections, the neck portion positioned between the engagement section and the free leg.

13. The bracket of claim 12 wherein the neck portion is positioned between the projections when the closing spring is in the closed position and the engagement section is engaged by the projections.

14. The bracket of claim 8 wherein an opening is formed in the free leg of the closing spring adjacent to the tongue, the opening receiving a tool to disengage the tongue from the projections.

15. The bracket of claim 8 wherein the tongue is formed from a portion of the free leg partially cut therefrom and bent substantially perpendicular to the free leg, thereby forming an opening within the free leg.

16. The bracket of claim 8 wherein the projections each have an apex edge and a top side which extends from the apex edge away from the arch wire slot.

17. The bracket of claim 8 wherein the closing spring has a thickness and the projections and the arch wire slot are spaced apart by at least the thickness of the closing spring.

18. The bracket of claim 8 further comprising a base plate having a top side and a bottom side, the bottom side capable of being attached to the tooth and the top side attached with respect to the wings.

19. A bracket for an orthodontic treatment, the bracket comprising:

a structure for operative connection to a tooth, the structure including two wings spaced from one another to form a gap, each wing forming an elongate wire slot for receiving an arch wire, the wire slot dividing each wing into a first and second section;

a closing spring anchored to the structure and comprising an arc extending over the first sections and a free leg adjoining the arc, the closing spring being movable between an open position, in which the arch wire slot is freely accessible, and a closed position, in which the free leg covers the arch wire slot;

each first section includes a projection extending into the gap such that the projections are spaced apart by a distance; and the free leg of the closing spring includes a tongue depending at an angle therefrom, the tongue including an engagement section having a width which is less than the gap between the first wing sections and greater than the distance between the projections, the engagement section of the tongue being engaged by the projections when the closing spring is in the closed position to retain the spring in the closed position.

* * * * *